United States Patent [19]

Yoshida et al.

[11] Patent Number: 4,724,258
[45] Date of Patent: Feb. 9, 1988

[54] ADULT T CELL LEUKEMIA VIRUS ANTIGEN POLYPEPTIDE

[75] Inventors: Mitsuaki Yoshida; Haruo Sugano, both of Tokyo, Japan

[73] Assignee: Juridical Foundation, Japanese Foundation for Cancer Research, Tokyo, Japan

[21] Appl. No.: 696,035

[22] Filed: Jan. 29, 1985

[30] Foreign Application Priority Data

Feb. 3, 1984 [JP] Japan .................................. 59-16951
Mar. 12, 1984 [JP] Japan .................................. 59-46686

[51] Int. Cl.$^4$ ........................ C07K 13/00; C12P 21/02
[52] U.S. Cl. ...................................... 530/350; 530/806; 530/808; 530/820; 530/825; 435/68; 435/70; 935/47; 935/65; 424/89
[58] Field of Search .................... 260/112 R, 112.5 R; 435/68

[56] References Cited

U.S. PATENT DOCUMENTS 4,520,113 5/1985 Gallo et al. ........................... 424/89
4,572,800 2/1986 Shimizu et al. ...................... 424/88

FOREIGN PATENT DOCUMENTS 0113078 7/1984 European Pat. Off. .
0152030 8/1985 European Pat. Off. .
WO84/04327 11/1984 PCT Int'l Appl. .

OTHER PUBLICATIONS

Kiyokawa et al., "Env Protein of HTLU" *PNAS*, 81 1984, pp. 6202-6206.
Franchini et al., "HTLV Transcrips-Leukemia" *PNAS* 81 1984, pp. 6707-6711.
Weinstock et al., "Open Reading Frame Expression Vectors" *PNAS*, vol. 80, 1983, pp. 4432-4436.
Germino et al., "Use of Gene Fusion and Proteins--Protein Interaction . . . Plasmid R6K" *PNAS*, vol. 80, 1983, pp. 6848-6852.
Casadaban et al., *J. Bacteriology*, vol. 143(2) 1980, pp. 971-980.
Yoshida et al., *PNAS* 79, 1982, pp. 2031-2035.
Manzari et al., *PNAS* 80, 1983, pp. 1574-1578.
Oroszlan et al., *PNAS* 79, 1982, pp. 1291-1294.
Hinuma et al., *PNAS* 78(10) 1981, pp. 6476-6480.
Hattori, et al., Gann, 74, No. 6, Dec. 1983; 790-3.
Seiki, et al., P.N.A.S., 80, Jun. 1983: 3618-22.

*Primary Examiner*—Morton Foelak
*Assistant Examiner*—Garnette D. Draper
*Attorney, Agent, or Firm*—Fitzpatrick, Cella, Harper & Scinto

[57] ABSTRACT

Recombinant plasmids are constructed by inserting a DNA fragment containing the env gene of adult T cell leukemia virus or a part thereof into a vector DNA. Microorganisms are transformed with the recombinant plasmid and thereafter cultured to express the peptide. The antigen polypeptide encoded by the env gene is useful for the detection and diagnosis of adult T cell leukemia.

2 Claims, 1 Drawing Figure

ADULT T CELL LEUKEMIA VIRUS ANTIGEN POLYPEPTIDE

BACKGROUND OF THE INVENTION

The present invention relates to a recombinant plasmid wherein a DNA fragment containing the env gene of adult T cell leukemia virus [referred to as ATLV hereinafter; ATLV is a synonym of human T cell leukemia virus (HTLV)] or a part thereof is incorporated, a microorganism containing the plasmid and a process for producing an antigen polypeptide encoded by the env gene of adult T cell leukemia virus or a part thereof or a fused protein of the peptide and an enzyme such as $\beta$-galactosidase using the microorganism.

Adult T cell leukemia virus is a C-type retrovirus isolated from patients with adult T cell leukemia (hereinafter referred to as ATL) [Yoshida, et al.: Proc. Natl. Acad. Sci., USA, 79, 2031–2036 (1982)]. There are numerous reports that ATL patients have a poor prognosis and that efficacious treatment does not exist leading to a 50% mortality rate within 10 months.

In recent years, an antibody which reacts specifically with cultured MT-1 cells derived from ATL has been shown to exist in the serum of ATL patients [Hinuma, et al., Proc. Natl. Acad. Sci., USA, 78, 6476–6480 (1981)]. The existence of this antibody has been confirmed subsequently in most ATL patients and the corresponding antigens are called ATL-associated antigen (hereinafter referred to as ATLA). It has been found that the antibody specific for ATLA (hereinafter referred to as Anti-ATLA antibody) exists in 25% of normal, healthy adults in areas with a high incidence of ATL. It has also been shown that the distribution of cases possessing the anti-ATLA antibody corresponds to the regions with high ATL incidence. Furthermore, it has been shown that ATLA is mainly the virus antigen of this ATLV. The existence of ATLV genome in the peripheral blood lymphocytes of patients has been established. ATLV has also been detected by culturing the lymphocytes of normal people who are positive to anti-ATLA antibody.

There is a very close correlation between ATL and ATLV, and ATLV is considered to be the causative virus of ATL. Though the route by which infection occurs is still unknown, it has been proved that transfusion of blood is one of the routes. As 25% of healthy people in areas with a high incidence of ATL are anti-ATLA antibody positive, the likelihood of their being carriers of ATLV is extremely high, which means that they must be avoided as blood donors for transfusion.

Therefore, detection of the presence of anti-ATLA antibody will enable avoidance of transfusions from the carriers and early ATL detection. At the present time, detection of anti-ATLA antibody is conducted using acetone fixed slides of cultured cells derived from ATL. However, a simpler, faster method of anti-ATLA antibody detection and earlier ATL diagnosis are desirable.

The present inventors have studied about a method for providing one of the ATLA which is useful for diagnosis of ATLV infection, prevention of ATLV infection and treatment of leukemia caused by ATLV in a large amount and at low cost. As the result, it has now been found that an ATLV antigen peptide encoded by the env gene of the ATLV genome or a part thereof, or a fused protein of the peptide and an enzyme such a $\beta$-galactosidase can be accumulated in a large amount by culturing a microorganism containing a recombinant DNA which is obtained by incorporating a DNA fragment containing the env gene and a gene coding for the enzyme into a vector DNA using recombinant DNA techniques, and the present invention has been completed.

It has already been reported that one of the products derived from the env gene is a glycosylated protein (gp 62) having a molecular weight of 62,000 [Hattori, et al.: Gann, 74, 790–793 (1983)] and the entire DNA sequence of ATLV was determined by the present inventors [Japanese Patent Application No. 214287/82, Proc. Natl. Acad. Sci., USA, 80, 3618–3622 (1983)].

SUMMARY OF THE INVENTION

The present invention provides a recombinant plasmid wherein a DNA fragment containing the env gene of ATLV or a part thereof is incorporated, a microorganism containing the plasmid, and a process for producing an antigen polypeptide encoded by the env gene of ATLV or a part thereof using the microorganism. The production of ATLV antigen peptide encoded by the env gene or a part thereof or a fused protein of the peptide and an enzyme such as $\beta$-galactosidase using a microorganism has been achieved first by the present invention.

DESCRIPTION OF THE INVENTION

Figure 1:
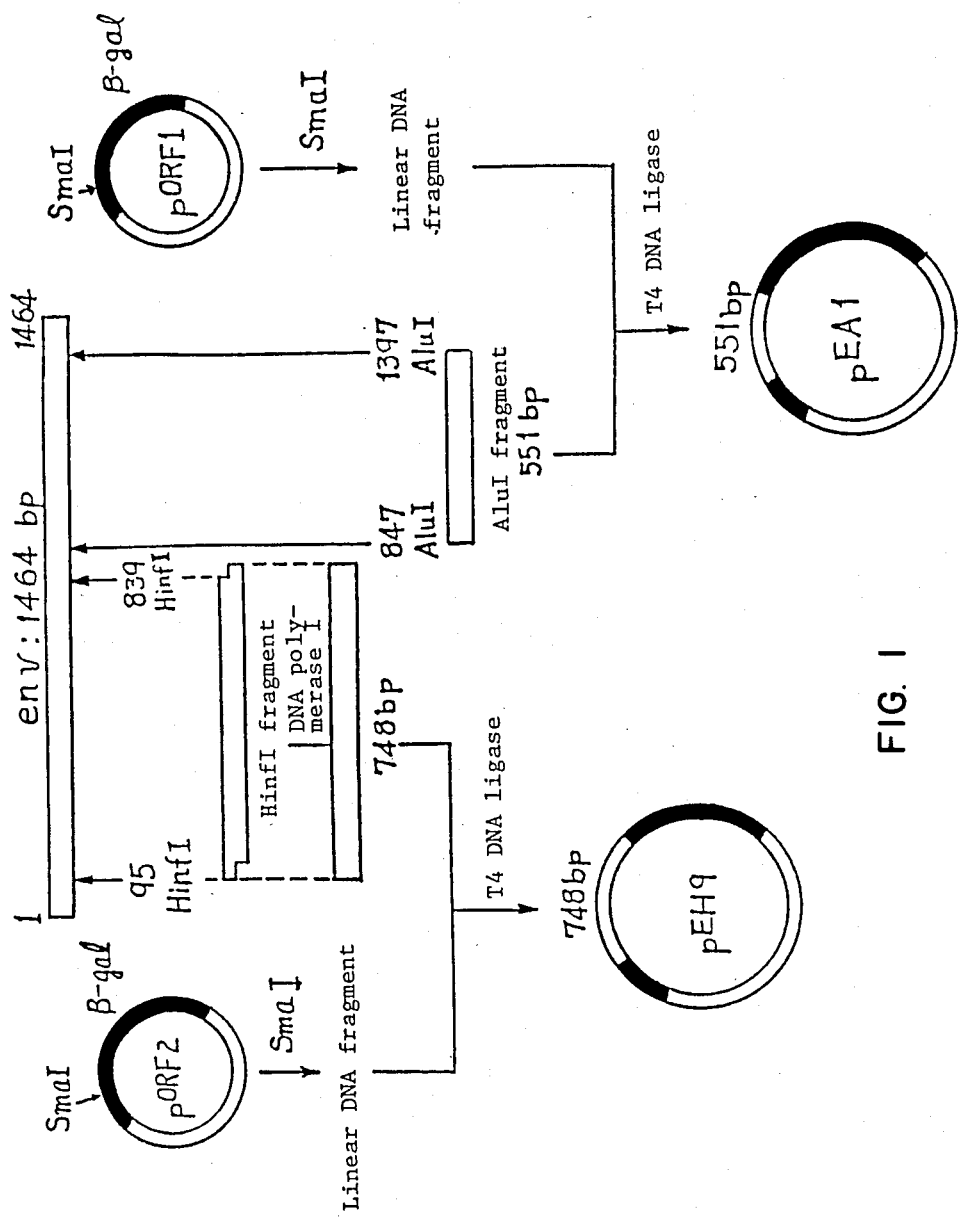
FIG. 1 is a flow sheet showing the construction of the plasmid of the present invention.

The present invention provides a recombinant plasmid wherein a DNA fragment containing the env gene of ATLV or a part thereof is-incorporated, a microorganism containing the plasmid, and a process for producing an antigen polypeptide encoded by the env gene of ATLV or a part thereof using the microorganism.

The construction of the recombinant plasmid of the present invention is carried out in the following manner.

The recombinant plasmid can be constructed by incorporating a DNA containing the env gene of ATLV or a part thereof into a vector DNA using recombinant DNA techniques.

As the DNA containing the env gene of ATLV or a part thereof, for example, pATK08 cloned by Seiki, et al. [Seiki, et al., Proc. Natl. Acad. Sci., USA, 80, 3618–3622 (1983)] is employable. The genome of ATLV consists of the LTR at both ends and at least four genes, namely, gag, pol, env and pX. Since the protein encoded by the env gene is assumed to be a glycosylated protein responsible for infectiousness of ATLV, it is expected that the protein is employable for the diagnosis of ATLV infection, prevention of ATLV infection, and treatment of leukemia caused by ATLV. The use of the protein itself as a vaccine is also expected.

pATK08 is a clone containing the entire env gene and can be used as a source of the DNA fragment containing the env gene.

Any vector DNA can be utilized, provided that the inserted DNA can be expressed in a microorganism. Examples of the preferred plasmids are pORF1 and pORF2 which are described in Weinstock, et al.: Proc. Natl. Acad. Sci., USA, 80, 4432–4436 (1983) and can be prepared by the method described in the reference.

Recombination of a DNA containing the env gene of ATLV or a part thereof and a vector DNA, for example, pORF1 or pORF2 can be carried out using general recombinant DNA techniques in which both DNAs are digested with restriction enzymes followed by ligation using T4 DNA ligase. Ligation may be conducted by a method employing fill-in reaction with DNA polymerase I·Klenow fragment or a method using a DNA linker.

In the case of pATK08 and pORF2 mentioned as examples, as shown in FIG. 1, recombinant plasmid pEH9 can be constructed by digesting the env gene of pATK08 with restriction enzyme HinfI, changing the ends to blunt ends with DNA polymerase I (Klenow fragment) and inserting the DNA fragment into a SmaI site of pORF2. pEA1 can be obtained by digesting the env gene of pATK08 with restriction enzyme AluI and inserting the DNA fragment into pORF1. As illustrated in FIG. 1, a DNA fragment of 748 base pairs (referred to as bp hereinafter) located in the first half of the env gene is incorporated in pEH9 and a DNA fragment of 551 bp located in the second half of the env gene is incorporated in pEA1.

The reaction conditions necessary for the above-described preparation of the recombinant plasmid are generally as follows. DNA digestion with restriction enzymes is normally carried out by 15 minutes-24 hours digestion of 0.1-100 μg of DNA, at 18°-42° C., preferably 32°-38° C., using 0.1-300 units, preferably 1-3 units, of restriction enzyme per 1 μg of DNA in 2-200 mM, preferably 10-14 40 mM Tris-HCl (pH 6.0-9.5, preferably pH 7.0-8.0), 1-150 mM NaCl and 2-20 mM, preferably 5-10 mM $MgCl_2$. The reaction is terminated by heating at 55°-75° C., preferably 63°-70° C., for 5-30 minutes. The restriction enzymes may be inactivated by reagents such as phenol and diethylpyrocarbonate. Ligation of DNA fragments is conducted at 1°p14 37° C., preferably 3°-20° C., for 15 minutes to 72 hours, preferably 2-20 hours using 0.1-10 units of T4 DNA ligase in 2-200 mM, preferably 10-70 mM Tris-HCl (pH 6.0-9.5, preferably pH 7.0-8.0), 2-20 mM, preferably 5-10 mM $MgCl_2$, 0.1-10 mM, preferably 0.5-2 mM ATP and 1-50 mM, preferably 5-10mM dithiothreitol.

Purification of the DNA fragments, recombinant plasmids, etc. is carried out by agarose gel electrophoresis.

ATLV antigen polypeptide encoded by the env gene or a part thereof is obtained by culturing a transductant obtained by introducing a recombinant plasmid such as pEH9 or pEA1 into a microorganism.

It is desirable to use *Escherichia coli* as the host microorganism and MH3,000 or TK1046 derived from the *Escherichia coli* K-12 strain [G.M. Weinstock, et al., Proc. Natl. Acad. Sci., USA, 80, 4432–4436 (1983)] is preferably used.

Transduction is carried out in accordance with the method of S.N. Cohen, et al.: Proc. Natl. Acad. Sci., USA, 69, 2110 (1972). Transductants can be screened by the formation of blue colony by fused protein with βgalactosidase.

Expression of ATLV antigen peptide by the transductant strain is detected, for example, by culturing the strain in L-Broth, suspending the collected cells in a buffer solution consisting of 125 mM Tris-HCl (pH 6.8), 2% SDS, 0.7M 2-mercaptoethanol and 0.0025% bromophenol blue, heating the suspension, subjecting the centrifuged supernatant fluid to electrophoresis in 7% polyacrylamide gel containing SDS and staining the gel with Coomassie Blue.

The polypeptide detected in this way is ascertained to give specific immune agglutination with patient serum, which indicates that it has the properties of ATLV antigen peptide.

Isolation of the plasmids from the microorganisms is carried out in accordance with the method of H.C. Birnboim, et al.: Nucleic Acids Research 7, 1513 (1979).

Transductants of pEH9 and pEA1 have been deposited with the American Type Culture Collection, U.S.A. under the Budapest Treaty as *Escherichia coli* CI9 ATCC 39591 and *Escherichia coli* CI10 ATCC 39592, respectively.

Certain specific embodiments of the invention are illustrated by the following representative examples.

EXAMPLE 1

Construction of plasmid pEH9 which contains the first half of env gene

Plasmid pATK08 was isolated from *Escherichia coli* (*E. coli*) ATCC 32246 by the method of Seiki, et al. described in Proc. Natl. Acad. Sci., USA, 80, 3613–3622, 1983. 20 μg of pATK08 was dissolved in 200 μl of a buffer solution consisting of 50 mM NaCl, 6 mM Tris-HCl (pH 7.5), 6 mM MgCl2 and 2 mM 2-mercaptoethanol. 60 units of restriction enzyme HinfI (product of Takara Shuzo Co., the restriction enzymes hereinafter are all products of Takara Shuzo Co., unless otherwise specified) was added and reaction was carried out at 37° C. for 3 hours. The reaction product was subjected to 1% agarose gel electrophoresis and staining with 5 μg/ml ethidium bromide to detect DNA fragments. A DNA fragment of about 750 bp was recovered. About 1 μg of the thus recovered DNA fragment was added to 100 μl of a solution consisting of 50 mM Tris-HCl (pH 7.5), 5 mM $MgCl_2$, 2 mM dithiothreitol, 0.1 mM dATP, 0.1 mM dTTP, 0.1 mM dGTP and 0.1 mM dCTP. 3 units of DNA polymerase I (Klenow fragment) [product of Bethesda Research Laboratories (referred to as BRL hereinafter)] was added and reaction was carried out at 15° C. for 1 hour. By this reaction, the staggered end of the DNA fragment formed by the cleavage with HinfI was repaired to a blunt end. The reaction product was subjected to 1% agarose gel electrophoresis to recover a DNA fragment of 748 bp.

Separately, vector plasmid pORF2 was linearized by the method described in the reference mentioned above using SmaI.

0.5 μg of the DNA fragment of 748 bp and 5 μg of the linearized pORF2 were added to 0.5 ml of a solution consisting of 50 mM Tris-HCl (pH 7.5), 10 mM $MgCl_2$, 20 mM dithiothreitol and 1 mM ATP. 5 units of T4 DNA ligase (product of Takara Shuzo Co.) was added and ligation reaction was carried out at 14° C. for 3 days. The reaction solution was subjected to phenol extraction to remove proteins and *E. coli* MH3,000 activated by the conventional method (Weinstock, et al., Proc. Natl. Acad. Sci., USA, 80 4432–4436, 1983) was transduced using the thus obtained solution. The transduced *E. coli* MH3,000 was dispersed on an agar medium containing L-Broth consisting of 10 g/l Bactotrypton, 5 g/l yeast extract and 5 g/l NaCl, 10 mg/ml 5-bromo-4-chloro-3-indolyl-β-D-galactoside (referred to as XG hereinafter) and 15 g/l agar, and cultured at 25° C. for 2 days. The strain wherein the desired DNA fragment was inserted and which produces a fused protein containing βgalactosidase formed a blue colony by the decomposition of XG. A blue colony selected was cultured using L-Broth at 25° C. for 3 hours. 100 μg of a plasmid was recovered from the cultured cells by the method described in H.C. Birnboim, et al.: Nucleic Acids Research 7, 1513, 1979. The plasmid was named plasmid pEH9. It was confirmed that pEH9 had the structure containing the first half of the env gene as presumed by analyzing the base sequence of the DNA inserted in the plasmid and the base sequence around the DNA by the method of Maxam, et al. [A.M. Maxam & W. Gilbert, Methods in Enzymology, 65, 499–560 (1980)].

EXAMPLE 2

Construction of plasmid pEA1 which contains the second half of env gene

Plasmid pATK08 was isolated by the same method as described in Example 1.

20 μg of pATK08 was dissolved in 200 μl of a buffer solution consisting of 50 mM NaCl, 6 mM Tris-HCl (pH 7.5), 6 mM $MgCl_2$ and 2 mM 2-mercaptoethanol. 60 units of restriction enzyme AluI was added and reaction was carried out at 37° C. for 3 hours. The reaction product was subjected to 1% agarose gel electrophoresis and staining with 5 μg/ml ethidium bromide to detect DNA fragments. A DNA fragment of about 551 bp was recovered.

Separately, pORF1 was linearized by the same method as described in Example 1.

0.5 μg of the DNA fragment of 551 bp and 5 μg of the linearized pORF1 were added to 0.5 ml of a solution consisting of 50 mM Tris-HCl (pH 7.5), 10 mM $MgCl_2$, 20 mM dithiothreitol and 1 mM ATP. 5 units of T4 DNA ligase was added and ligation reaction was carried out at 14° C. for 3 days.

The reaction solution was subjected to phenol extraction to remove proteins and *E. coli* MH3,000 activated by the method described above was transduced using the thus obtained solution. The transduced *E. coli* MH3,000 was dispersed on the agar medium described above containing L-Broth and 10 mg/ml XG, and cultured at 25° C. for 2 days. The strain wherein the desired DNA fragment was inserted and which produces a fused protein containing β-galactosidase formed a blue colony by the decomposition of XG. A blue colony selected was cultured by the same method as described in Example 1 to obtain a plasmid from the cultured cells. The plasmid was named plasmid pEA1. It was confirmed that pEA1 had the structure containing the second half of the env gene as presumed by the same method as described in Example 1.

EXAMPLE 3

Mass expression of pEH9 and pEA1

Propagation of the microorganism containing a recombinant plasmid bearing the incorporated genes of β-galactosidase and env such as pEH9 or pEA1 is inhibited by the mass expression of the plasmid, because of the toxicity of the fused protein encoded by the plasmid. The following treatment was conducted for the mass expression of pEH9 and pEA1.

According to the method described in G.M. Weinstock, et al., Proc. Natl. Acad. Sci. USA, 80, 4432–4436, 1983, *E. coli* TK1046 which has a low-temperature sensitive gene activating the promoter incorporated into the plasmid was transduced with pEH9 and pEA1, respectively. Transduced *E. coli* TK1046 strains were cultured in 25 ml of L-Broth at 30° C. to an $OD_{600}$ value of about 0.2–0.3 and additionally at 37° C. for one hour. Cells were harvested and suspended in a buffer solution consisting of 125 mM Tris-HCl (pH 6.8), 2% SDS, 0.7M 2-mercaptoethanol and 0.0025% bromophenol blue. The amount of the buffer solution is 1/70 of the volume of the used medium. The suspension was heated at 100° C. for 3–5 minutes. After centrifugation at 10,000 rpm for 5 minutes, the supernatant fluid was subjected to electrophoresis in 7% polyacrylamide gel containing 0.1% SDS and the gel was stained with Coomassie Blue. As the result, the main band of the protein for pEH9 was detected at the position of a molecular weight of about 156K and for pEA1 at about 149K. These are named protein EH9 and EA1. The main band is considered to be the desired fused protein because the band is not detected in a cell transduced with only a vector.

EXAMPLE 4

Preparation of antibodies to protein EH9 and EA1 containing a part of env protein The protein bands of molecular weights of 156K and 149K detected in Example 3 were cut and recovered. The gel was disrupted in 2 ml of a solution consisting of 50 mM Tris-HCl (pH 7.5) and 0.1% SDS using potter-type glass homogenizer. The suspension of the gel and protein was mixed with an equal amount of Freund adjuvant (product of Difco). 2 ml of the mixed suspension was injected subcutaneously (booster) in the back of a rabbit (4 months old male) at intervals of two weeks and the antibody value in the serum was determined weekly. The antibody value was determined by the method wherein the serum was diluted two-fold, labelled EH9 and EA1 were subjected to immunoprecipitation and the precipitate was isolated with polyacrylamide gel. A serum showing antibody value increased by 1000 times was obtained by about 3 times of booster.

EXAMPLE 5

Detection of the antibody in human serum using protein EH9 and EA1.

It was examined in the following manner whether the fused protein prepared by *E. coli* as described in Example 4 can be used to detect anti-env antibody considered to be present in human serum positive to ATLA antibody.

About 0.5 μg of EH9 and EA1 partially purified by acrylamide gel electrophoresis according to the method described in Example 3 was adsorbed on a nitrocellulose membrane (product of Millipore) in a form of spot of 0.5 cm diameter, followed by drying at room temperature. After the nitrocellulose membrane was shaked in 5 ml of bovine serum at room temperature for one hour, excess solution was removed from the membrane and 1 ml of gradiently diluted serum of ATL patient was reacted with the membrane at room temperature for 3 hours. The nitrocellulose membrane was then washed with a solution [50 mM Tris-HCl (pH 7.5), 0.3M NaCl] containing 0.1% Tween 20 (product of Wako Junyaku Kogyo Co., Ltd.), reacted with 5 μl of anti-human Ig antibody labelled with $^{125}I$ (product of Amersham) by a conventional method (H. Towbin, et al., Proc. Natl. Acad. Sci., 76 4350–4354, 1979) and exposed on X ray film.

As the result, the anti-env antibody carried by ATL patient reacted with fused protein EH9 or EA1 on the nitrocellulose membrane an th1e human antibody molecule reacted with $^{125}$I-anti-human Ig antibody to give a black spot on the film.

By using the reaction, env-specific antibody could be determined with the sensitivity ten times higher than the antibody value determination by the conventional fluorescent antibody technique. It is possible to analyze a large amount of sample rapidly at less cost and with a higher sensitivity by precipitation reaction radioimmunoassay method and ELISA method (method for the detection of antigen-antibody using enzyme-binding antibody) using mass-produced EH9 or EA1 protein as an antigen, or the method using test papers smeared with these proteins under the properly controlled conditions for detecting antibodies.

What is claimed is:

1. An antigen polypeptide product encoded by a 748 bp HinfI-cleaved ATLV env gene or a 551 bp AluI-cleaved ATLV env gene fragment, which is produced by the the process of culturing in a medium a microorganism selected from the group consisting of *Escherichia coli* CI9 ATCC 39591 and *Escherichia coli* CI10 ATCC 39592, accumulating said product in the culture medium and recovering the product therefrom.

2. A fused protein product encoded by a DNA fragment which contains a 748 bp HinfI-cleaved ATLV env gene or a 551 bp AluI-cleaved ATLV env gene fragment, inserted in a SmaI cleavage site of β-galactosidase gene, which is produced by the process of culturing in a medium a microorganism selected from the group consisting of *Escherichia coli* CI9 ATCC 39591 and *Escherichia coli* CI10 ATCC 39592, accumulating said product in the culture medium and recovering the product therefrom.

* * * * *

UNITED STATES PATENT AND TRADEMARK OFFICE
CERTIFICATE OF CORRECTION

PATENT NO. : 4,724,258

DATED : February 9, 1988

INVENTOR(S) : MITSUAKI YOSHIDA, ET AL.

It is certified that error appears in the above-identified patent and that said Letters Patent is hereby corrected as shown below:

Column 3, line 29, "10-14 40 mM" should read:
--10-40 mM--

Column 3, line 35, "1°p14 37°C.," should read:
--1°-37°C.,--

Column 7, line 1, "an thle" should read: --and the--

Column 7, line 18, "Hinfi-cleaved" should read:
--HinfI-cleaved--.

Column 8, line 2, delete "the" (second occurrence).

Signed and Sealed this

Twelfth Day of July, 1988

Attest:

DONALD J. QUIGG

Attesting Officer

Commissioner of Patents and Trademarks